(12) United States Patent
Mrue

(10) Patent No.: US 8,071,106 B2
(45) Date of Patent: Dec. 6, 2011

(54) TOPICAL FORMULATION CONTAINING LATEX OF FRACTION THEREOF, AND COSMETIC TREATMENT METHOD

(75) Inventor: Fatima Mrue, Goiania-Go (BR)

(73) Assignee: Pele Nova Biotecnologia S.A., Terenos-MS (BR)

( * ) Notice: Subject to any disclaimer, the term of this patent is extended or adjusted under 35 U.S.C. 154(b) by 460 days.

(21) Appl. No.: 12/091,228

(22) PCT Filed: Oct. 26, 2006

(86) PCT No.: PCT/BR2006/000231
§ 371 (c)(1),
(2), (4) Date: Apr. 23, 2008

(87) PCT Pub. No.: WO2007/048215
PCT Pub. Date: May 3, 2007

(65) Prior Publication Data
US 2008/0279885 A1    Nov. 13, 2008

(30) Foreign Application Priority Data

Oct. 27, 2005  (BR) ...................................... 0504797

(51) Int. Cl.
*A61K 36/02* (2006.01)
(52) U.S. Cl. ................................................. 424/195.18
(58) Field of Classification Search .................. None
See application file for complete search history.

(56) References Cited

U.S. PATENT DOCUMENTS

| | | | | |
|---|---|---|---|---|
| 4,060,081 A | * | 11/1977 | Yannas et al. | 623/15.12 |
| 5,080,889 A | * | 1/1992 | Katada et al. | 424/63 |
| 5,519,046 A | * | 5/1996 | Noda et al. | 514/413 |
| 6,087,310 A | * | 7/2000 | Henkel | 510/138 |
| 6,129,956 A | * | 10/2000 | Morra et al. | 427/535 |
| 6,284,233 B1 | | 9/2001 | Simon et al. | |
| 6,413,526 B1 | | 7/2002 | Bazin et al. | |
| 6,589,544 B2 | * | 7/2003 | Leong | 424/402 |
| 2003/0180335 A1 | * | 9/2003 | Ohmori et al. | 424/401 |
| 2004/0197361 A1 | * | 10/2004 | Oguchi et al. | 424/401 |
| 2005/0042191 A1 | * | 2/2005 | Travkina et al. | 424/70.7 |
| 2006/0099161 A1 | * | 5/2006 | Nakane et al. | 424/65 |
| 2006/0289834 A1 | * | 12/2006 | Doisaki et al. | 252/397 |
| 2007/0202233 A1 | * | 8/2007 | Kato et al. | 426/577 |
| 2007/0231354 A1 | * | 10/2007 | Sogabe et al. | 424/401 |

FOREIGN PATENT DOCUMENTS

| | | | |
|---|---|---|---|
| JP | 62-063507 | | 3/1987 |
| JP | 06247838 | * | 9/1994 |
| RO | 61338 | | 6/1976 |

OTHER PUBLICATIONS

Website document entitled 'A Brief Natural History of Latex Rubber Allergy', 4 pages, download on Feb. 1, 2011 from http://www.immune.com/rubber/nrl.html.*

* cited by examiner

Primary Examiner — Christopher R. Tate
(74) Attorney, Agent, or Firm — Fitch, Even, Tabin & Flannery

(57) ABSTRACT

The present invention refers to a topical formulation containing natural latex or fraction thereof, for topical application, aiming to provide skin regeneration. It particularly refers to a formulation comprising latex from plants of the families Euphorbiaceae, such as *Hevea brasiliensis*, Apocinaceae, such as guava and sorb, Compositae such as guayule, Caricaceae such as papaya, or one of its fractions, whose topical application provides the skin with regeneration benefits, such as whitening or elimination of senile spots, increase in turgor, improved texture, shine and resilience.

13 Claims, No Drawings

TOPICAL FORMULATION CONTAINING LATEX OF FRACTION THEREOF, AND COSMETIC TREATMENT METHOD

FIELD OF THE INVENTION

The present invention refers to a topical formulation containing natural latex or a fraction thereof, for topical application, aiming to provide skin regeneration.

It particularly refers to a formulation comprising latex from plants of the families Euphorbiaceae, such as *Hevea brasiliensis*, Apocinaceae, such as guava and sorb, Compositae such as guayule, Caricaceae such as papaya, or a fraction of the latex, whose topical application provides the skin with regeneration benefits, such as whitening or elimination of senile spots, increase in turgor, improved texture, shine and resilience.

BACKGROUND OF THE INVENTION

Skin is the human body largest organ, having an important protective and sensorial function between the organism and the external environment. It protects the organism against dehydration, loss of fluids and proteins, maintains and dissipates heat, avoids the entrance of microorganisms such as bacteriae, viruses, fungi and parasites, and of harmful chemicals.

Ageing signals are easily noted on the skin, such as the appearance of wrinkles, lines of expression, lentigoes (senile spots), malasma and chloasma (pregnant women), loss of resilience, texture, shine, reduction in thickness, higher rigidity and drying up.

Besides the age of the person, sun exposure is a key factor inducing skin ageing. Among the means used to repair damages caused by early ageing, there are surgical treatments, dermal abrasion, chemical peelings, chemical cauterization, criosurgery, filling injections with collagen, metacrylates and hyaluronic acid, botulinic toxic, laser application etc. Although these procedures show good results, chemical treatment methods for aged skin or its prevention are still rare. The main products with huge popular consumption are those absorbing ultraviolet rays, commercialized as sun protectors.

The skin contains an intricate net of elastin fibers which is responsible for its elastic properties. Under excessive solar exposure, the elastic fibers becomes hyperplastic, unorganized and interrupted. This process is known as actinic elastosis and is the main cause of wrinkles, decoloration and lack of energy. As new fibroblasts, endothelial cells and keratinocytes are formed, skin tends to regenerate, but this route gets slower with ageing, the dermis-epidermis junction becomes plain, resulting in less general mechanical resistance, and there is a reduction in the number of cells and vessels supplying the skin. As a result, the skin becomes thinner, less resilient, providing the appearance of wrinkles and more opaque aspect.

In view of the above, regenerating or anti-skin ageing products have been proposed. Usually, solutions have been to use various additives in common cosmetic compositions, so as to efficiently provide energy to an aged skin, such as polyhydric alcohols (e.g. glycerin or sorbitol), hyaluronic acid, collagen, elastin, humidifying agents (amino acids, salts of lactic acid, sodium pyrrolidone carboxylate or urea), intercellular lipids (sphyngolipids, phospholipids or cholesterol), lipid simulators (olive oil, jojoba oil or squalene); cell activating agents (vitamins A, C, E or their derivatives, vitamin F or linoleic acid, vitamin H or glutathione), animal extracts (placenta liquid or royal jelly), etc. The use of titanium powder or talc powder is also known in surface treatment formulations, to make malasma or wrinkles less evident by mere make-up.

Specifically concerning skin coloring, the use of whitening agents is known, such as L-ascorbic acid and its derivatives, hydroquinone, glutathione and colloidal sulfur derivatives, aiming to eliminate or prevent abnormal deposition of melanine pigments. They are however deficient due to their weak inhibitory effect over melanine production, the presence of odors and precipitate formation. Therefore, their individual use in cosmetics brings a whitening effect with low efficiency.

The search for solutions for skin ageing, as we can be seen, is an activity in full development. Within this context, the present invention provides and efficient and simple topical formulation, providing regenerating and healing effects to the skin, differently from what is currently known.

DESCRIPTION OF THE INVENTION

The invention refers, in a first aspect, to a formulation characterized by comprising natural latex or a fraction thereof, particularly from plants of the families Euphorbiaceae, such as *Hevea brasiliensis* (rubber tree), Apocinaceae, such as guava and sorb, Compositae such as guayule, Caricaceae such as papaya, and a film-forming agent.

As used herein, the mention to natural latex refers to latex taken from the plant, be it stabilized or not, polymerized or not. The mention to a "fraction of the latex" means serum obtained from natural latex (e. g. by coagulation), or just the solid part of the latex obtained e. g. by centrifugation, or their mixtures in any proportion.

In a particulate embodiment, natural latex used for the invention is as traditionally treated, i.e. taken from the plant/tree and prepared for later use, e. g. by keeping it in an ice bath until the addition of anticoagulants, buffers as phosphate or glycerin-phosphate salts, borate or other salts from weak acids or buffering bases stabilizing pH at 10-12. Not excluding any alternative, buffered natural latex submitted to centrifugation is used in the composition of the invention, particularly appropriate latex emulsions thus being obtained with 45% and 65% of polyisoprenoids, fully or partially providing the feature of forming the film of the formulation.

In another particular embodiment, serum or its liquid phase is taken off from a natural coagulated latex, and used to prepare the formulation of the invention, particularly in the presence of a film-forming agent.

As used in this document, a film-forming agent is any compound or group of compounds which, added to latex, favors film-forming. Said agent prevents or helps prevent latex coagulation while in contact with the skin, not substantially affecting the polymerization of the compounds contained in the latex. Advantageously, polymucosaccharides such as glucosaminoglycans provide such property, particularly one or more from hyaluronic acid, hyaluronates of metals such as sodium, heparan, condroitin-sulphate, acaran sulphate, keratan sulphate or dermatan sulphate.

Also considered as film-forming agents, not excluding any others, are natural polysaccharides such as starch, amylose and amylopectin, cellulose and its derivatives, chitosan, alginate, agar, agarose and their mixtures among themselves or with others.

The formation of a film from the polymerized latex itself, in an alternative embodiment of the invention, fully or partially supplies such a feature of film formulation of the invention.

The formulation of the invention may optionally contain appropriate carriers and excipients, such as buffer, surfactants, sun protectors, preserving agents, etc.

Advantageously, the formulation of the invention may also contain additives and active principles having intimate contact with the skin during the permanence of the film, interacting with it in addition to latex per se. Particular examples, not excluding any others, are: humidifiers (such as glycerol), antioxidants (such as vitamin C, coenzyme Q, tocopherols as vitamin E), depigmenting agents (such as hydroquinone, kojic acid, azelaic acid, liquiritin, N-acetyl-cisteaminephenol), proteins (such as collagen type 1), cell renewal agents (such as retinoic acid), exfoliating agents (such as glycolic, tannic, citric, salicylic acids, alpha-hydroxy acids).

Within the formulation of the invention, quantities of 40-60% by weight of latex or its fraction, such as polyisoprenoids themselves, are appropriate and may be present in emulsions at about 35-75%, particularly 45-65% by weight. Quantities of 0.05-5% by weight of one or more film formation agents are also appropriate, particularly 0.1-2% by weight.

It is believed that, after applied to the skin, the formulation of the invention is able to stimulate the formation of new blood vessels on the dermis (angiogenesis), improving local irrigation and consequently the perfusion of nutrients and oxygen into the skin, stimulating the production of collagen fibers, elastic fibers, glucosamineglycans, regenerating and/or delaying its ageing and eliminating or reducing the formation of wrinkles, lines of expression and senile spots of normal or aged skin.

The formulation of the invention, when applied as a thin layer over the skin, as a gel, emulsion, cream, ointment, lotion, spray or any other presentation, in contact with the oxygen in the air and water evaporation, forms a thin clear, semipermeable, polymeric layer, nearly imperceptible to the eyes, e. g., in a particular embodiment, by polymerization of the polyisoprenoids present in latex, over the applied area. Such polymeric membrane formed on the skin and with intimate contact with it maintains a large number of intact micelles from the natural latex, which will be the carrier for active principles through the stratum corneum of the epidermis.

By means of this innovative, practical and efficient form of transdermal transport, various active principles are carried, the most important of which is the angiogenic factor naturally secreted by trees during the extraction process of natural latex, providing the skin with cosmetic qualities.

The angiogenic factor carried by transdermal transport by micelles stimulates the formation of new blood vessels on the dermis, increasing perfusion and consequently improving nutrition and oxygenation of skin layers. Therefore, fibroblasts are stimulated to proliferate and increase the production of substances from the extracellular matrix, such as collagens, elastic fibers and glucosamineglycans. Fibroblasts are simultaneously induced to release metalloproteinases, acting to re-shape collagens, elastin and especially crosslinked proteins, partially responsible for the lack of resilience of the skin. Thus, the skin is again well nourished, reestablishing its resilience and turgor and improving the shine and texture of regenerated skin. Such action is potentialized and facilitated by the joint action of proteins, antioxidizing polyphenols, tocopherols, vitamin C, coenzyme Q, molecules from natural latex reacting and blocking the action of free radicals produced by skin metabolism and sun ray action, potentializing and facilitating the regenerating action and delaying ageing.

Another aspect of the invention is a cosmetic treatment method, characterized by comprising the following steps:

Applying over the region of the skin to be treated a formulation comprising natural latex or a fraction thereof and a film-forming agent;

film formation;

permanence of said film in contact with the skin for a desired time period;

removal of said film.

This method favors intimate contact between the formed membrane and the skin, providing the transmission of both active principles contained in the latex (or fraction thereof) and the ones optionally added to it, therefore effecting, by means of its removal, micropeeling of the outer surface layer, by removing dead cells and providing cell renewal on that surface.

The presence of natural depigmenting factors in natural latex, such as antioxidant polyphenols, polyisoprenes and coenzyme Q, and the dermal peeling made during the removal of the formed membrane, particularly act to reduce or eliminate senile spots (lentigoes), malasma and chloasma (pregnant spots), pathognomic for aged skins.

The method of the invention covers both the forced removal (by the user, by a third person or by an equipment with that purpose) of the film formed by the formulation containing latex, as well as its slow removal, e. g. after a shower, with no interference from the user, from a third person or from an equipment for this purpose.

EXAMPLES

A particular embodiment of the invention is described below, given as a mere example, with no limitation to the scope of the invention different from what is established in the attached claims.

The formulation below was prepared:

centrifuged natural latex emulsion at 60% polyisoprenoids—85 g;

1% sodium hyaluronate—15 g;

heparan—1 mg.

Example 1

The formulation was applied to the skin on the back of the left hand of four patients more than 40 years old, two men and two women, with clear signs of aged skin, such as reduced resilience, texture and shine, presence of wrinkles and senile spots. The opposite side hand was used as a control, by applying usual hydrating cream to it. Application was daily with removal of the polymeric membrane after 24 hours for two weeks. Patients have been evaluated quarterly for three months. On the left hand, treated with the formulation, clear signs of regeneration were found, such as substantial disappearance of senile spots, improvement in turgor, texture, shine and skin resilience.

It is well understood that, with the support of the teachings and the example disclosed herein, a person skilled in the art is able to make equivalent variations of the invention, by mere change in manner without escaping from the scope of the attached claims, once reaching foreseen results for similar functions as provided by the different aspects of the invention.

The invention claimed is:

1. A topical dermal formulation, comprising between 40% and 60% by weight of a natural latex or fraction thereof from plants of families selected from the group consisting of Euphorbiaceae, Apocinaceae, Compositae, Caricaceae, or mixtures thereof, and between 0.05% and 5% by weight of one or more natural film-forming agents, wherein the one or more film-forming agents is selected from the group consisting of a mucopolysaccharide, a glucosamineglycan, hyaluronic acid, hyaluronate, sodium hyaluronate, heparan, condroitin-sulphate, acaran sulphate, keratin sulphate, and dermatan sulphate.

2. The formulation of claim 1, wherein the latex is from plant *Hevea brasiliensis*.

3. The formulation of claim 1, wherein said latex is in the form of an emulsion containing 35-75% by weight of latex or fraction thereof.

4. The formulation of claim 1, wherein said fraction of latex is substantially centrifuged latex.

5. The formulation of claim 1, wherein the fraction of latex is substantially latex serum.

6. The formulation of claim 1, wherein the formulation includes said film-forming agent in an amount between 0.05 and 5% by weight of the formulation.

7. The formulation of claim 1, wherein the amount of said film-forming agent is between 0.1 and 2% by weight of the formulation.

8. The formulation of claim 1, comprising cosmetically and/or pharmaceutically acceptable carriers or excipients.

9. The formulation of claim 1, comprising one or more additives chosen from the group consisting of hydroquinone, kojic acid, azelaic acid, liquiritin, N-acetyl-cisteaminephenol, glycolic acid, retinoic acid, vitamin E, vitamin C, collagen type 1, coenzyme Q, tannic, citric, salicylic, alpha-hydroxy acids, and mixtures thereof.

10. The formulation of claim 1, comprising one or more sun protectors.

11. The formulation of claim 1, wherein the formulation is presented as gel, emulsion, cream, ointment, lotion or spray.

12. A cosmetic treatment method comprising:
applying the formulation of claim 1 over a region of skin to be treated;
forming a film on the skin;
leaving the film in contact with the skin for a desired period of time; and
removing the film from the skin.

13. The cosmetic treatment method of claim 12, wherein applying the formulation on affected area of the skin is effective for elimination or reduction of senile spots, melasma or chiliasm.

\* \* \* \* \*